US00PP20088P2

(12) United States Plant Patent
Goetz

(10) Patent No.: US PP20,088 P2
(45) Date of Patent: Jun. 9, 2009

(54) ***FUCHSIA* PLANT NAMED 'GOETZYOL'**

(50) Latin Name: *Fuchsia×hybrida*
Varietal Denomination: Goetzyol

(75) Inventor: Wolfram Goetz, Herbrechtingen (DE)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 12/070,573

(22) Filed: Feb. 19, 2008

(51) Int. Cl.
*A01H 5/00* (2006.01)

(52) U.S. Cl. ..... Plt./300
(58) Field of Classification Search ..... Plt./300
See application file for complete search history.

*Primary Examiner*—June Hwu
(74) *Attorney, Agent, or Firm*—C. A. Whealy

(57) ABSTRACT

A new and distinct cultivar of *Fuchsia* plant named 'Goetzyol', characterized by its compact and upright growth habit; freely branching plant habit; dark pink-colored flowers; early and freely flowering habit; and good garden performance.

1 Drawing Sheet

Botanical designation: *Fuchsia×hybrida*.
Cultivar denomination: 'GOETZYOL'.

BACKGROUND OF THE INVENTION

The present invention relates to a new and distinct cultivar of *Fuchsia*, botanically known as *Fuchsia×hybrida* and hereinafter referred to by the name 'Goetzyol'.

The new *Fuchsia* is a product of a planned breeding program conducted by the Inventor in Herbrechtingen, Germany. The objective of the breeding program is to create new compact *Fuchsia* cultivars with attractive flower color.

The new *Fuchsia* originated from a cross-pollination made by the Inventor in 2000 in Herbrechtingen, Germany of a proprietary selection of *Fuchsia×hybrida* identified as code number 45/97, not patented, as the female, or seed, parent with a proprietary selection of *Fuchsia×hybrida* identified as code number 16/99, not patented, as the male, or pollen, parent. The new *Fuchsia* was discovered and selected by the Inventor as a single flowering plant within the progeny of the stated cross-pollination in a controlled environment in Herbrechtingen, Germany in 2001.

Asexual reproduction of the new *Fuchsia* by terminal cuttings in a controlled environment in Herbrechtingen, Germany since the autumn of 2001, has shown that the unique features of this new *Fuchsia* are stable and reproduced true to type in successive generations.

SUMMARY OF THE INVENTION

The cultivar Goetzyol has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Goetzyol'. These characteristics in combination distinguish 'Goetzyol' as a new and distinct cultivar of *Fuchsia*:

1. Compact and upright growth habit.
2. Freely branching plant habit.

3. Dark pink-colored flowers.
4. Early and freely flowering habit.
5. Good garden performance.

Plants of the new *Fuchsia* differ primarily from plants of the female parent selection in the following characteristics:

1. Plants of the new *Fuchsia* are more compact than plants of the female parent selection.
2. Flowers of plants of the new *Fuchsia* are more upright than flowers of plants of the female parent selection.

Plants of the new *Fuchsia* differ primarily from plants of the male parent selection in the following characteristics:

1. Plants of the new *Fuchsia* are more compact than plants of the male parent selection.
2. Plants of the new *Fuchsia* have smaller leaves than plants of the male parent selection.

Plants of the new *Fuchsia* can be compared to plants of the cultivar Goetztil, not patented. Plants of the new *Fuchsia* and the cultivar Goetztil differ in the following characteristics:

1. Plants of the new *Fuchsia* are more compact than plants of the cultivar Goetztil.
2. Plants of the new *Fuchsia* are not as upright as plants of the cultivar Goetztil.
3. Plants of the new *Fuchsia* and the cultivar Goetztil differ in flower color.

BRIEF DESCRIPTION OF THE PHOTOGRAPHS

The accompanying colored photographs illustrate the overall appearance of the new *Fuchsia*, showing the colors as true as it is reasonably possible to obtain in colored reproductions of this type. Colors in the photographs may differ slightly from the color values cited in the detailed botanical description which accurately describe the colors of the new *Fuchsia*.

The photograph at the bottom of the sheet comprises a side perspective view of a typical flowering plant of 'Goetzyol' grown in a container.

The photograph at the top of the sheet is a close-up of typical flowers and leaves of 'Goetzyol'.

DETAILED BOTANICAL DESCRIPTION

The aforementioned photographs and following observations, measurements and values describe plants grown in Bonsall, Calif., under commercial practice during the spring and early summer in a polyethylene-covered greenhouse with day temperatures ranging from 16° C. to 35° C. and night temperatures ranging from 13° C. to 21° C. Plants were grown for about 15 weeks in 15-cm containers and were pinched. In the following description, color references are made to The Royal Horticultural Society Colour Chart, 1995 Edition, except where general terms of ordinary dictionary significance are used.

Botanical classification: *Fuchsia×hybrida* cultivar Goetzyol.

Parentage:

*Female, or seed, parent.*—Proprietary selection of *Fuchsia×hybrida* identified as code number 45/97, not patented.

*Male, or pollen, parent.*—Proprietary selection of *Fuchsia×hybrida* identified as code number 16/99, not patented.

Propagation:

*Type.*—By terminal cuttings.

*Time to initiate roots, summer.*—About two to three weeks.

*Time to initiate roots, winter.*—About three weeks.

*Time to produce a rooted young plant, summer.*—About six weeks.

*Time to produce a rooted young plant, winter.*—About eight weeks.

*Root description.*—Fine, fleshy; white to light brown in color.

*Rooting habit.*—Freely branching; moderately dense.

Plant description:

*Plant and growth habit.*—Compact and upright plant habit; rounded in overall shape. Freely branching; about five to six primary branches per plant. Moderately vigorous growth habit.

*Plant height.*—About 26 cm.

*Plant diameter.*—About 28 cm.

Lateral branch description:

*Length.*—About 13 cm.

*Diameter.*—About 3 mm.

*Internode length.*—About 2.2 cm.

*Strength.*—Strong.

*Aspect.*—Initially upright to outwardly arching.

*Texture.*—Pubescent; minute hairs.

*Color, young.*—145C.

*Color mature.*—199A.

Foliage description:

*Arrangement.*—Opposite, simple.

*Length.*—About 5.4 cm.

*Width.*—About 3.5 cm.

*Shape.*—Ovate.

*Apex.*—Acute.

*Base.*—Obtuse.

*Margin.*—Entire with irregular shallow points.

*Texture, upper and lower surfaces.*—Smooth, glabrous.

*Venation pattern.*—Pinnate; arcuate.

*Color.*—Developing foliage, upper and lower surfaces: 146A. Fully expanded foliage, upper surface: 147A; venation, 147B. Fully expanded foliage, lower surface: 147B; venation, 147C.

*Petiole.*—Length: About 1.7 cm. Diameter: About 3 mm. Texture, upper and lower surfaces: Pubescent; minute hairs. Color, upper surface: 177D. Color, lower surface: 147C.

Flower description:

*Flower arrangement and habit.*—Single axillary flowers. Flowers initially upright and then somewhat pendulous. Flowers not fragrant. Freely flowering habit with typically about 50 open flowers and flower buds per plant.

*Natural flowering season.*—In southern California, plants flower from early spring to fall; flowering continuous during this period. Plants begin flowering about four to six weeks after planting. Flowers last about five to six days on the plant. Flowers not persistent.

*Flower diameter.*—About 4.5 cm; corolla diameter, about 1.5 cm.

*Flower height.*—About 4.3 cm.

*Flower buds.*—Shape: Elliptic. Length: About 3 cm. Diameter: About 1.3 cm. Color: 61C.

*Petals.*—Arrangement: Four or five in a single whorl. Length: About 1.5 cm. Width: About 1.5 cm. Shape: Obovate. Apex: Rounded. Base: Acute. Margin: Entire. Texture, upper and lower surfaces: Smooth, glabrous. Color: When opening, upper surface: 80A. When opening, lower surface: 81C. Fully opened, upper surface: 80B; towards the base, 55B; color becoming closer to 84B with development. Fully opened, lower surface: 81C; towards the base, 62A; color becoming closer to 84C with development.

*Sepals.*—Arrangement: Calyx star-shaped with four sepals fused at the base. Length: About 2 cm. Width: About 1 cm. Shape: Ovate. Apex: Acute. Margin: Entire. Texture, upper and lower surfaces: Smooth, glabrous. Color: When opening and fully opened, upper surface: 57B. When opening and fully opened, lower surface: 57A.

*Peduncles.*—Length: About 2.6 cm. Diameter: About 1 mm. Angle: About 45° from vertical. Strength: Strong. Texture: Pubescent; minute hairs. Color: 145B.

*Reproductive organs.*—Stamens: Quantity: Ten per flower. Filament length: About 2.2 cm. Filament color: 63B to 63C. Anther shape: Oval. Anther size: About 1 mm by 2 mm. Anther color: 165B. Pollen amount: Moderate. Pollen color: 158B. Pistils: Quantity: One per flower. Pistil length: About 4.5 cm. Style length: About 3.5 cm. Style color: 65D. Stigma shape: Rounded. Stigma color: 158D. Ovary color: 146B.

*Seed/fruit.*—Seed and fruit development have not been observed on plants of the new *Fuchsia*.

Garden performance: Plants of the new *Fuchsia* have been observed to have good garden performance and to tolerate wind, rain and temperatures from about 10° C. to about 32° C.

Pathogen/pest resistance: Plants of the new *Fuchsia* have not been observed to be resistant to pests and pathogens common to *Fuchsia*.

It is claimed:

1. A new and distinct *Fuchsia* plant named 'Goetzyol' as illustrated and described.

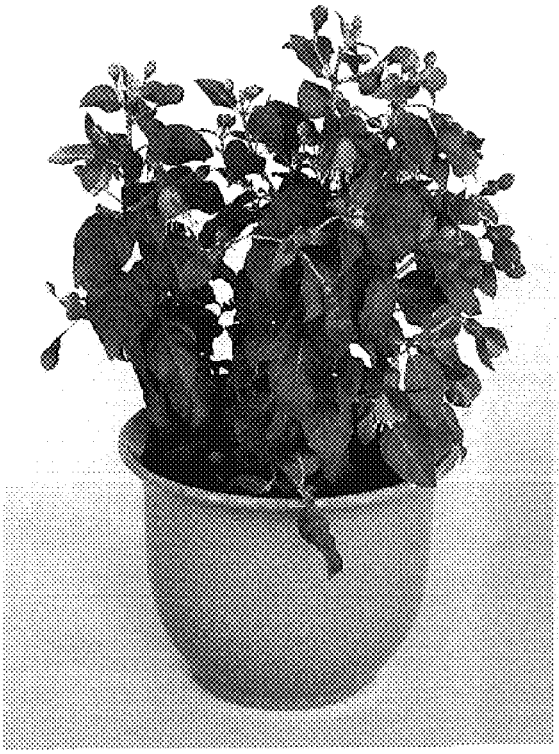
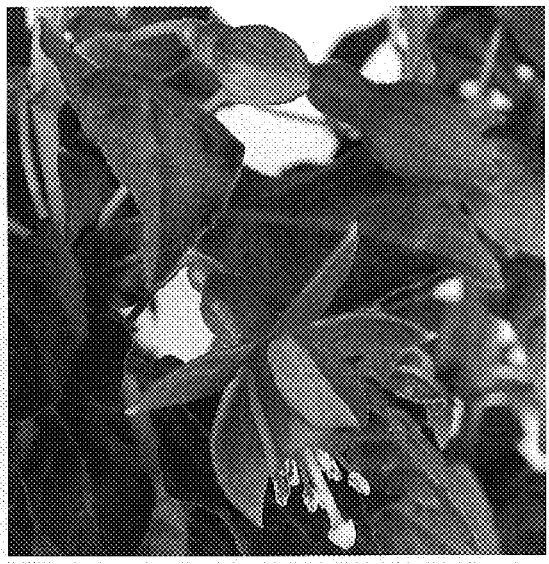

* * * * *